United States Patent [19]
Reinhold, Jr.

[11] Patent Number: 5,465,727
[45] Date of Patent: Nov. 14, 1995

[54] TWELVE-LEAD PORTABLE HEART MONITOR

[75] Inventor: Herbert E. Reinhold, Jr., Rockville, Md.

[73] Assignee: Brunswick Biomedical Corporation, Marlboro, Mass.

[21] Appl. No.: 303,755

[22] Filed: Aug. 26, 1994

[51] Int. Cl.⁶ .................................................. A61B 5/0404
[52] U.S. Cl. .......................... 128/710; 128/696; 128/904; 128/644
[58] Field of Search ................................. 128/710, 696, 128/639, 640, 644, 904

[56] References Cited

U.S. PATENT DOCUMENTS

| | | |
|---|---|---|
| 3,058,458 | 10/1962 | Daneman . |
| 3,776,228 | 12/1973 | Semler . |
| 3,792,700 | 2/1974 | Sarnoff et al. . |
| 3,888,240 | 6/1975 | Reinhold, Jr. et al. . |
| 3,910,260 | 10/1975 | Sarnoff et al. . |
| 3,938,507 | 2/1976 | Sarnoff et al. . |
| 4,004,577 | 1/1977 | Sarnoff . |
| 4,122,843 | 10/1978 | Zdrojkowski . |
| 4,318,412 | 3/1982 | Stanly et al. . |
| 4,573,474 | 3/1986 | Scibetta . |
| 4,608,987 | 9/1986 | Mills . |
| 4,658,830 | 4/1987 | Sarnoff . |
| 4,763,660 | 8/1988 | Kroll et al. . |
| 4,862,896 | 9/1989 | Reinhold, Jr. et al. . |
| 4,889,134 | 12/1989 | Greenwold et al. . |
| 4,957,109 | 9/1990 | Groeger et al. . |
| 5,016,636 | 5/1991 | Kulakowski . |
| 5,184,620 | 2/1993 | Cudahy et al. . |
| 5,224,479 | 7/1993 | Sekine . |
| 5,339,823 | 8/1994 | Reinhold, Jr. . |

FOREIGN PATENT DOCUMENTS 8909020  10/1989  WIPO .

Primary Examiner—Lee S. Cohen
Assistant Examiner—Stephen Huang
Attorney, Agent, or Firm—Cushman Darby & Cushman

[57] ABSTRACT

An apparatus for obtaining electrical heart activity of an individual in a form capable of producing a twelve-lead electrocardiogram of an individual, said apparatus including: a right arm electrode; a left arm electrode; at least one leg electrode; a portable electrode support having a plurality of at least seven precordial electrodes fixed thereon. The at least seven precordial electrodes extend laterally across the support so as to assume different lateral positions across the human chest when the support is positioned over the chest. Circuitry is carried by the support in electrically connected relation to the electrodes and is capable of selectively operating a selected six of the plurality of precordial electrodes at positions which correspond to the six Wilson precordial leads for the individual. The circuitry is constructed and arranged to convert the electrical heart activity of the individual obtained by the electrodes into a form capable of producing a twelve-lead electrocardiogram.

29 Claims, 3 Drawing Sheets

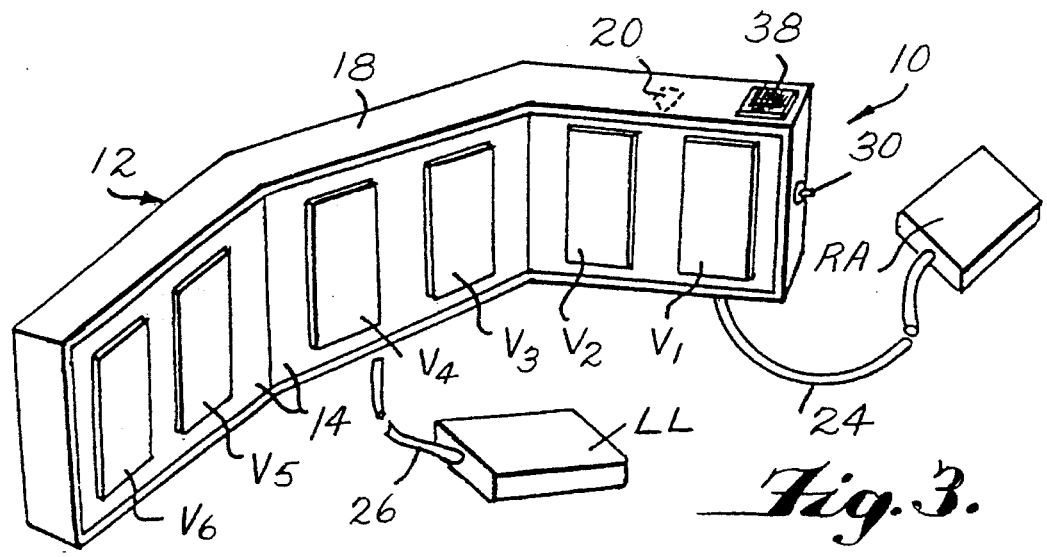
Fig. 3.
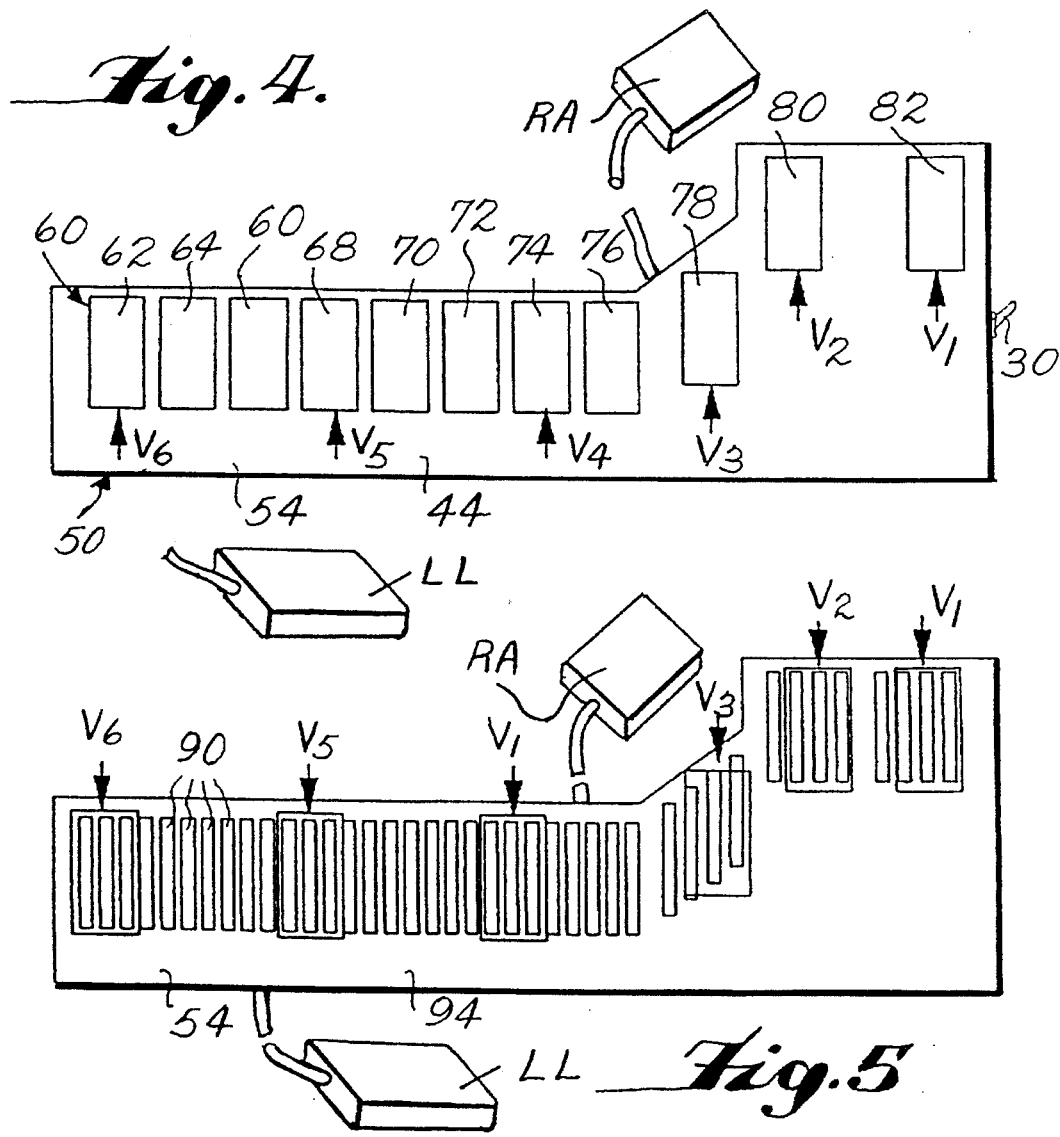
Fig. 4.
Fig. 5.

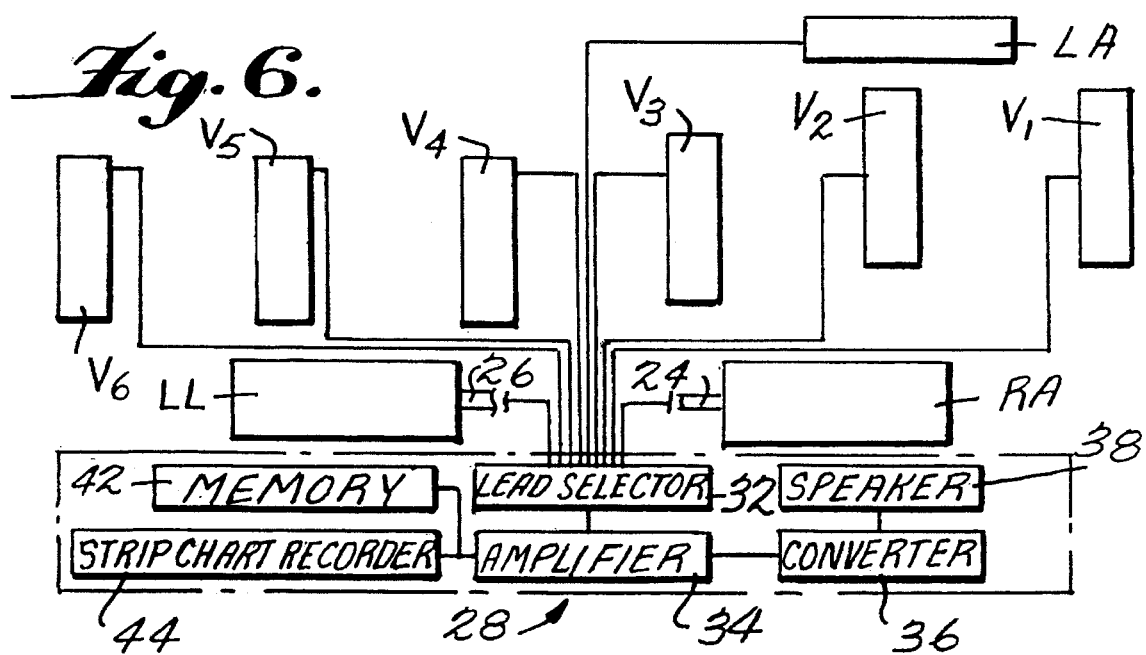

1

TWELVE-LEAD PORTABLE HEART MONITOR

BACKGROUND OF THE INVENTION

1. Field of the Invention

This invention relates to heart monitors and more particularly to heart monitors of the portable type.

2. Background Information

One example of a portable heart monitor of the type herein contemplated is disclosed in commonly assigned U.S. Pat. No. 3,938,507. The monitor of the '507 patent is provided with a pair of electrodes which are configured so as to be conveniently and comfortably held within the armpits of a user in accordance with the teachings of U.S. Pat. No. 3,792,700. The preferred use of the device is in the method disclosed in U.S. Pat. Nos. 3,910,260, 4,004,577, and 4,658,830. As disclosed in the aforesaid patents, heart monitors may be used in conjunction with medicaments contained within auto-injectors for enabling a designated coronary-prone individual to self-administer arrhythmia and thrombolytic treatment drugs during the early minutes or hours of the onset of heart attack symptoms at a time before the individual can be hospitalized or reached by an ambulance crew. For this use, it is important that the monitor be capable of simple, but effective, connection with the user so as to acquire the electrical activity of the heart of the user in a form capable of transmission over a telephone line to a central source where sufficient intelligence is provided for aiding the individual in undertaking the self-administered treatment.

Portable heart monitors are also utilized as portable diagnostic tools. Typically, a portable heart monitor could be used by paramedics. In addition, such portable monitors are quite useful in physician house calls. Moreover, portable monitors can have many uses in hospitals as well.

A limitation on the two-electrode monitor disclosed in the aforesaid '507 patent is that it is capable essentially of providing only one lead out of the twelve leads which are conventionally provided by non-portable in hospital ECG machines, see, for example, U. S. Pat. No. 3,058,458. There have been attempts to build into portable monitoring devices the capability of monitoring more than one lead. For example, in commonly assigned U.S. Pat. No. 4,862,896, the two-electrode unit of the '507 patent was made adaptable to provide more than one lead by securing the electrodes in predetermined positions within the exterior of the monitor housing so as to achieve an additional modified precordial lead. Furthermore in commonly assigned U.S. Pat. No. 4,889,134, there is disclosed a portable heart monitor which embodies three electrodes so as to enable the user to obtain leads I, II, and III with the use of the device. Particularly, when the device is used in its diagnostic mode, it is desirable to provide a heart monitor which is capable of obtaining more than three leads.

In U.S. Pat. Nos. 5,224,479, 4,608,987, and 4,573,474 there is advantageously disclosed twelve lead portable monitors which include leads I, II, III, ARV, AVL, AVF, $V_1$, $V_2$, $V_3$, $V_4$, $V_5$, and $V_6$. In the aforementioned U.S. Patents, six Wilson precordial leads $V_1$–$V_6$ are carried by a vest or other types of harness.

A problem associated with the aforementioned conventional portable twelve lead device is that the six Wilson precordial leads $V_1$–$V_6$ are fixed at predetermined lateral positions on the harness, which positions are to correspond with the six anatomically defined Wilson precordial positions across the chest. It can be appreciated that in order to accommodate individuals of varying chest sizes, it is necessary to provide assemblies of correspondingly different sizes in order to establish correct placement of the precordial leads for those individuals. This is rather expensive and inefficient. While it is also possible to provide a single precordial electrode support that can have electrodes placed in different positions thereon (e.g., via snaps, VELCRO, or the like) according to the size of the individual, this is a time-consuming, tedious process, and incorrect placement of the electrodes by untrained individuals is possible.

SUMMARY OF THE INVENTION

It is an object of the present invention to provide a portable heart monitor which provides a plurality of electrodes from which six are to be selectively utilized, depending upon the chest size of the individual, as corresponding to the Wilson precordial positions for that individual. In accordance with the principles of the present invention, this objective is achieved by providing a heart monitor apparatus which includes an apparatus for obtaining electrical heart activity of an individual in a form capable of producing a twelve-lead electrocardiogram of an individual.

The apparatus includes a right arm electrode, a left arm electrode, at least one leg electrode, and a portable electrode support having a plurality of at least seven precordial electrodes fixed thereon. The precordial electrodes extend laterally across the support so as to assume different lateral positions across the human chest when the support is positioned over the chest. Circuitry is carried by the support in electrically connected relation to the electrodes and is capable of selectively operating a selected six of the plurality of precordial electrodes at positions which correspond to the six Wilson precordial leads for the individual. The circuitry being constructed and arranged to convert the electrical heart activity of the individual obtained by the electrodes into a form capable of producing a twelve-lead electrocardiogram.

While a selectivity of electrodes is discussed in U.S. Pat. No. 5,184,620 to Cudahy, which is hereby incorporated by reference, the selectivity of electrodes in this patent is provided only to accommodate for the event that one or more of the electrodes is not functioning properly or is not making proper contact with the chest. The Cudahy patent does not, however, provide multiple electrodes (e.g., at least seven) exteding laterally across the chest and which can be selectively used to accomodate different sized individuals (i.e., having different chest spans) to properly position the six precordial electrodes according to the six Wilson precordial leads for the individual.

It is a further object of the present invention to provide a twelve-lead heart monitoring device as above, but with better resolution and more exact positioning of the electrodes. To accomplish this object, the present invention provides an apparatus for obtaining electrical heart activity of an individual in a form capable of producing a twelve-lead electrocardiogram of an individual. The apparatus includes a right arm electrode, a left arm electrode, at least one leg electrode, a portable electrode support having a plurality of contact members fixed thereon, the contact members extending laterally across the support so as to assume different lateral positions across the human chest when the support is positioned over the chest, a selected number of the contact members being selectively operable to function as six precordial electrodes at positions corresponding to the Wilson precordial leads for the individual, wherein at least one of the six precordial electrodes comprise more than one of the contact members, and circuitry provided in electrically connected relation to contact members and capable of selectively activating the selected number of the contact members to function as the six precordial electrodes at positions corresponding to the Wilson precordial leads for the individual, the circuitry constructed and arranged to convert the electrical heart activity of the individual into a form capable of producing a twelve-lead electrocardiogram.

It is also an object of the invention to provide a method of obtaining electric heart activity of the individual in accordance with the principles stated above. To accomplish this result, the method comprises the steps of applying a right arm electrode, a left arm electrode, and a leg electrode to the skin of the individual at locations which enable leads I, II, III, AVR, AVL and AVF to be obtained therefrom, engaging a plurality of at least seven precordial electrodes extending laterally across an electrode support with the skin of the chest so that the precordial electrodes assume different lateral positions across the chest, operating the right arm electrode, left arm electrode and leg electrode, and selectively operating a selected six of the plurality of precordial electrodes at positions corresponding to the six Wilson precordial leads for the individual.

As another object of the present invention there is another method comprising the steps of applying a right arm electrode, a left arm electrode and a left leg electrode to the skin of the individual at locations which enable leads I, II, III, AVR, AVL and AVF to be obtained therefrom; engaging a plurality of contact members extending laterally across an electrode support with the skin of the chest so that the contact members assume different lateral positions across the chest, operating the right arm electrode, left arm electrode, and leg electrode; and selectively operating a selected number of the contact members to function as six precordial electrodes at positions corresponding to the Wilson precordial leads for the individual, wherein at least one of the six precordial leads comprises more than one of the contact members.

These and other objects of the present invention will become more apparent during the course of the following detailed description and appended claims.

The invention may best be understood with reference to the accompanying drawings wherein an illustrative embodiment is shown.

BRIEF DESCRIPTION OF THE DRAWINGS

FIG. 3 is a top and generally frontal perspective view of the conventional apparatus;

FIG. 4 is a generally elevational view of the operative interior surface of a heart monitoring apparatus as modified according to the first embodiment of the present invention.

FIG. 5 is a generally elevational view of the operative interior surface of a heart monitoring apparatus as modified according to the second embodiment of the present invention.

FIG. 6 is a functional view of the electric circuit of the heart monitoring apparatus of the present invention.

DETAILED DESCRIPTION OF THE INVENTION

Figure 1:
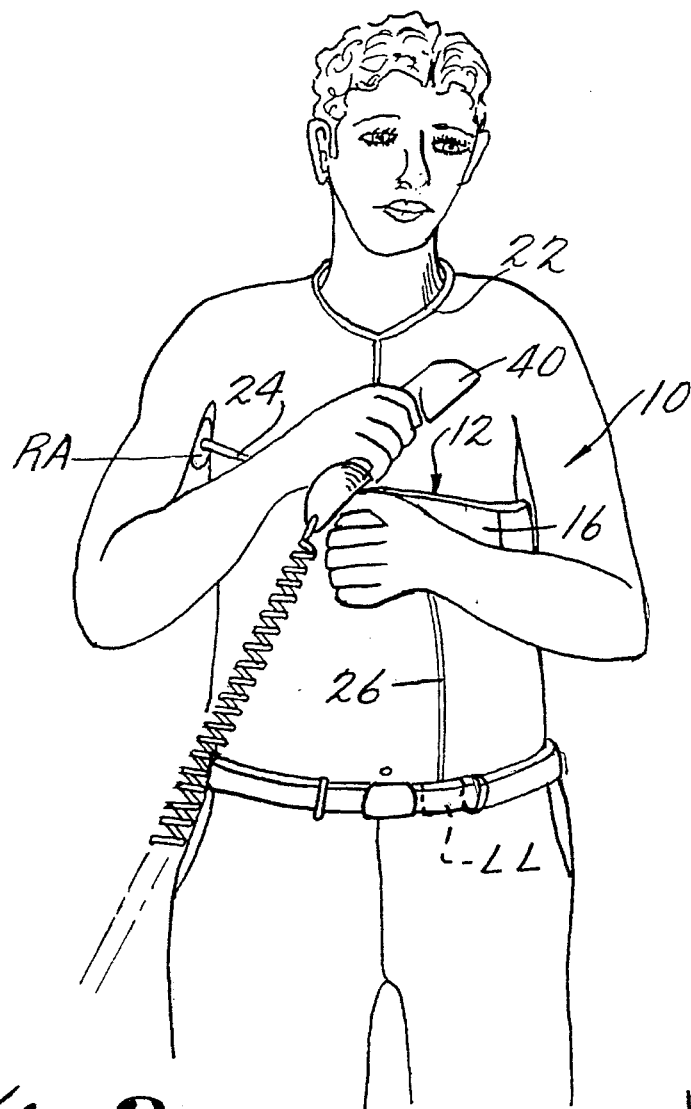
FIG. 1 is a pictorial view showing an individual using a conventional heart monitor apparatus for transmitting the audible signals derived therein over a telephone line to a central source.

Referring now more particularly to FIG. 1 of the drawings, there is shown therein a conventional heart monitor apparatus or device 10 as described in our co-pending U.S. patent application Ser. No. 07/925,912, the disclosure of which is hereby incorporated by reference. By way of example, and for best mode purposes, the principles of the present invention will be described in conjunction with the embodiment described in the aforementioned co-pending application. It is to be understood, however, that the present invention is not limited to the type of 12-lead monitor described therein, but can be applied to any portable 12-lead assembly (adhesive or non-adhesive) which utilizes six operative precordial leads carried by a support, harness, vest, or the like.

Figure 2:
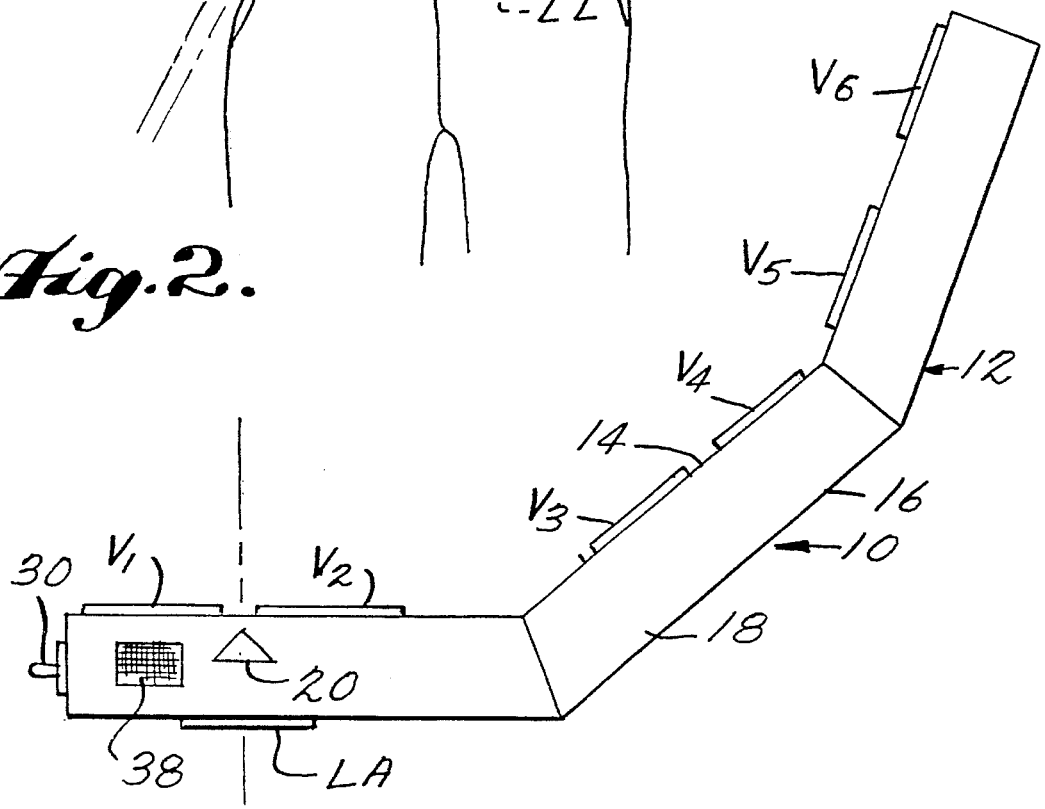
FIG. 2 is a top plan view of the conventional heart monitor apparatus shown in FIG. 1.

As described in the aforementioned application, a twelve lead device 10 includes a portable electrode support, generally indicated at 12, which may be in the form of a hollow housing consisting of three sections interconnected rigidly in angular relation with respect to one another. The support or housing 12 is of a size and angular shape to generally conform with the chest of a user. As best shown in FIG. 2, the concave side of the angularly related sections of the hollow housing 12 constitute an operatively interior surface 14 of the housing which is adapted to engage toward the chest of the user, while the opposite side constitutes an operatively exterior surface 16 by which human pressure, preferably from the individual, can retain the hollow housing in operative engagement with the chest.

In the aforementioned device, the portable electrode support 12 has fixed to the operative interior surface 14 thereof an array of six non-adhesive electrodes. The electrodes are designated by the reference characters $V_1$, $V_2$, $V_3$, $V_4$, $V_5$, and $V_6$, respectively, which correspond with the conventional six Wilson precordial leads also so designated. As best shown in FIG. 2, an arrow 18 or other similar indicia is placed on an upper edge surface 20 of the support 12 to provide the user with a breast bone reference point which enables the user to orient the support and, hence, the six precordial electrodes fixed thereon, in proper horizontal adjusted position with respect to the individual chest. In addition, a lanyard 22 is connected with the support 20 for engagement around the neck of the individual. The lanyard 22 is adjusted in length so that, when it is fully extended, the support is disposed in its proper vertical adjusted position. When the support 12 is disposed in its proper vertical and horizontal adjusted position, the six precordial electrodes can be engaged with the skin of the chest of the individual in an operative relation wherein the six electrodes correspond with the six Wilson precordial leads for that individual. This engagement is preferably made with the left arm and left hand of the individual applying human pressure to the support 12 generally in the manner indicated in FIG. 1. The upper left arm in the elbow area of the individual engages the portion of the support carrying electrodes $V_5$ and $V_6$ and the lower left arm and left hand extend over the operatively exterior surface 18 so as to apply an even pressure to retain each of the six precordial electrodes in operative relation.

The monitoring device 10 also includes a left arm electrode, designated by the reference character LA, which is suitably fixed to the operatively exterior surface 16 of the electrode support 12. The left arm electrode is preferably non-adhesive and constructed like the six precordial electrodes. As shown, the left arm electrode LA is disposed in a position to be engaged with the skin of the palm of the individual in an operative relation as the individual engages the six precordial electrodes in their operative relation. The left arm electrode LA is retained in its operative relation by the human pressure applied to the support 12 by the individual.

While the left arm electrode LA is shown and described above as having an operative relation with the skin of the palm, the location of the electrode on the support could be changed so that the operative relation could be with the skin of the forearm or any other part of the left arm of the individual which is applying pressure to the support 12 to retain the six precordial electrodes in their operative relation. It can also be appreciated that if the support 12 is provided with means for being strapped or otherwise secured to the individual, as in other conventional devices, the left arm electrode can be separately provided from the support. Where a separate left arm electrode is provided, it may be retained in the individual's left hand or in the individual's left armpit. Alternatively, the separate electrode (whether it be the leg electrode, right arm electrode, left arm electrode, etc.) can be retained adhesively on the skin as desired.

The aforementioned right arm electrode is designated by the reference character RA. This electrode is provided on the end of a wire 24 and preferably is constructed like the armpit electrode of the aforesaid '700 patent, the disclosure of which is hereby incorporated by reference into the present specification. The right arm electrode RA is operable to be engaged with the skin of the right armpit of the individual in an operative relation and to be retained therein by the right arm of the individual.

The monitoring device 10 also includes a leg electrode, such as a left leg electrode, which is designated by the reference character LL. The left leg electrode LL is preferably constructed in a manner similar to the right arm electrode RA on the end of a lead wire 26. The left leg electrode LL is adapted to be engaged with the skin of the waist of the individual, generally somewhat on the left side in an operative relation, as shown in FIG. 1. The left leg electrode can be retained in operative relation by a garment extending around the waist. Alternatively, the left leg electrode LL can be held in operative relation within a fold of skin in the waist area when the individual is in a sitting position, or adhesively secured to the skin.

As shown, the six precordial leads are positioned on the operatively interior surface 14 of the hollow housing or electrode support 12 in predetermined positions which are to correspond with the six anatomically defined Wilson precordial leads of the individual. In this regard, the array of electrodes on the electrode support 12 are positioned to fit the individual that is to use the monitor. This is done by manufacturing supports of different sizes in a manner somewhat similar to the way shoes are manufactured, or the support could be simply made in three sizes, large, medium and small, and the electrodes can be fixedly mounted thereon, as by adhesive, VELCRO, or suitable fasteners, in adjusted positions which are determined by fitting the support and electrodes to the individual.

It can be appreciated that, for the purposes of manufacturing costs, providing several different sized assemblies is quite expensive and inefficient. In addition, for a given sized support (e.g., small, medium or large) the relative positions of electrodes may need to be changed slightly from individual-to-individual. It can also be appreciated that where the six electrodes can be adjustably positioned on the support, the task of accurately positioning the electrodes on the support can be quite tedious.

In order to overcome these difficulties, the present invention provides a heart monitor apparatus or device having a plurality of electrodes or contacts from which six electrodes can be selected to correspond to the six Wilson precordial leads for the individual. As shown in FIG. 4, the device 50, in accordance with the principles of the present invention includes an electrode support 54, which can be a hollow housing as described above with respect to the conventional apparatus. Alternatively, the support 54 can be a flexible pad-like section which can conform to the skin of the chest when applied thereto, and can include a smaller housing for containing the circuitry, as described in the hereinbefore mentioned U.S. patent application Ser. No. 07/925,912. In the broadest aspects of the present invention, support 54 may be any harness, vest, or other structure capable of having a plurality of electrodes secured thereto.

As shown in FIG. 4, a plurality of electrodes 60 are fixed to the operatively interior surface 94 of the support. These electrodes extend laterally across the support so that they will assume different lateral positions across the human chest when the support is positioned over the chest. Six of the electrodes 60 are then selected to be used as corresponding to the six Wilson precordial leads for the individual using the device. For example, in the instance in which an individual with a relatively large chest span is to use the device, the electrodes 60 will be selected in accordance with locations which would correspond with the Wilson precordial positions for that individual. For instance, when a large sized individual is to use the device, the outermost electrodes 62 and 82, as shown by the arrows in FIG. 4, may be used as Wilson lead $V_6$ and $V_1$, respectively. FIG. 4 also shows that for such an individual, Wilson leads $V_2$, $V_3$, $V_4$, and $V_5$ may be obtained from electrodes 80, 78, 74, and 68, respectively. For another individual, such as one having a smaller chest, electrode 64 may be used as lead $V_6$, electrode 70 may be used as lead $V_5$, electrode 74 as lead $V_2$, electrode 76 as lead $V_3$, electrode 78 as lead $V_2$, and electrode 80 as lead $V_1$. These combinations of electrodes are merely exemplary, and it can be appreciated that any combination of such electrodes is possible.

While the embodiment of FIG. 4 shows eleven electrodes 60, it can be appreciated that the present invention is not limited to this number of electrodes. In fact, in accordance with the principles of the present invention, as few as seven electrodes can be provided, of which six are selected as the Wilson precordial electrodes to be used for a given individual. Of course, more than eleven electrodes can also be provided.

A second embodiment of the present invention is shown in FIG. 5. There, it can be seen that the portable electrode support 54 has a plurality of contact members 90 fixed thereon. The contact members extend laterally across the support so as to assume different lateral positions across the human chest when the support is positioned over the chest. A selected number of the contact members are operable to function as the six precordial electrodes at positions which correspond to the Wilson precordial leads for the individual using the device. As can be appreciated from FIG. 5, a plurality of contact members 90 may together comprise a single (electrode) or lead. For example, as shown, as viewed from left to right in FIG. 5, the boxed group of first three contact members are electrically connected so that together they comprise precordial electrode $V_6$. By providing electrodes which comprise a plurality of contact members, the device is capable of "fine-tuning" the position of each of electrode. For example, it is possible to move electrode $V_6$ slightly to the right in FIG. 5, simply by utilizing the second, third and fourth contact members, as viewed left to right, for the $V_6$ electrode. Similarly, all other precordial electrodes can be moved.

While three contact members comprise each electrode in FIG. 5, it is understood that the present invention is not so limited. For example, each electrode may comprise two contact members. It is also possible for each electrode to comprise a single contact member, in which case this embodiment becomes quite similar to that of the first embodiment. It is preferred, however, that at least one of the six precordial electrodes comprise more than one contact member so that it may be fine-tuned in the manner described.

Shown functionally in FIG. 6 and designated generally at 28 is the circuitry for use in the present invention. While it can be appreciated that similar circuitry is used for the aforementioned second embodiment, the circuitry in FIG. 6 is shown in conjunction with the first embodiment. The circuitry 28 is suitably electrically connected with all electrodes for the unit and is suitably battery energized and operated by a control 30, such as a manual switch suitably mounted on the exterior of the support. The circuitry is capable of selectively activating six of the precordial electrodes at positions which correspond to the six Wilson precordial leads for the individual. When the six selected precordial electrodes are in use, all others are non-functional. The desired six electrodes can be selected in a number of ways. For example, each of the electrodes 60 can be connected to circuitry 28 via conductors (e.g., wires) 90, and either mechanically (e.g., via a mechanical switch or pin connection) or electrically (e.g., via transistor circuitry) connected or disconnected from the circuitry. It can be appreciated by one skilled in the art that the means for connecting or disconnecting the desired electrodes can take many different forms, and that the configuration described is merely exemplary and in no way limiting to the scope of the invention.

The circuitry 28 preferably includes a lead selector 32, an example of which is disclosed in the aforesaid '458 patent, the disclosure of which is hereby incorporated by reference into the present specification. The lead selector can automatically select the combination of nine electrodes (including the selected six precordial electrodes) which will produce the twelve leads I, II, III, AVR, AVL, AVF, $V_1$, $V_2$, $V_3$, $V_4$, $V_5$, and $V_6$, in sequence when written for display in an electrocardiogram. The circuitry also preferably includes an amplifier component 34, a converter component 36, and a loud speaker 38. An example of these components of the circuitry is disclosed in the aforesaid '700 patent, the disclosure of which is hereby incorporated by reference into the present specification. Basically, the amplifier 34 amplifies the electric heart activity of the individual which is picked up by the electrodes selected by the lead selector 32. The converter 36 converts the output of the amplifier 34 into audible signals indicative of the electrical heart activity of the individuals which are emitted by the loud speaker.

The circuitry may also include a memory component 42. An example of a memory component is disclosed in the aforesaid '896 and '134 patents, the disclosures of which are hereby incorporated by reference into the present specification. The memory component 42 functions to store the output of the amplifier 34 in such a way that it can be retrieved on demand for use in producing a twelve-lead electrocardiogram on a strip chart recorder.

Finally, the circuitry 28 can include a strip chart recorder 44, which, like the circuitry is mounted on a suitable circuit board. An example of a strip chart recorder which can be utilized is the recorder Model 9240LP marketed by MFE Instruments, Division of Stocker and Vale, Inc. The strip chart recorder 44 is placed in the circuitry 28 so that it can produce a twelve-lead electrocardiogram either from the output of the amplifier 34 or the memory 42. Alternatively, the housing can have an exterior connector which would enable a separate strip chart recorder to be alternately connected with either the amplifier 34 or the memory 42 or such a separate strip chart recorder could be connected by a wire directly to the housing.

It thus will be seen that the objects of this invention have been fully and effectively accomplished. It will be realized, however, that the foregoing preferred specific embodiment has been shown and described for the purpose of this invention and is subject to change without departure from such principles. Therefore, this invention includes all modifications encompassed within the spirit and scope of the following claims.

What is claimed is:

1. An apparatus for obtaining electrical heart activity of an individual in a form capable of producing a twelve-lead electrocardiogram of an individual, said apparatus including:

a right arm electrode;

a left arm electrode;

at least one leg electrode;

a portable electrode support having at least seven precordial electrodes fixed thereon, said at least seven precordial electrodes extending laterally across the support so as to assume different lateral positions across a human chest when said support is positioned over the human chest; and circuitry provided in electrically connected relation to said right arm electrode, said left arm electrode, said at least one leg electrode, and said precordial electrodes, said circuit being capable of selectively operating a selected six of said at least seven precordial electrodes at positions corresponding to six Wilson precordial leads for the individual, said circuitry being constructed and arranged to convert the electrical heart activity of the individual obtained by said electrodes into a form capable of producing a twelve-lead electrocardiogram.

2. An apparatus according to claim 1, wherein said at least one leg electrode is a left leg electrode, said right arm electrode, said left arm electrode, and said left leg electrode being constructed so as to be operable to be applied onto skin of the individual at locations such that the circuitry can obtain leads I, II, III, AVR, AVL, and AVF therefrom, and wherein said selected six precordial electrodes enable said circuitry to obtain leads $V_1$, $V_2$, $V_3$, $V_4$, $V_5$ and $V_6$ therefrom.

3. An apparatus according to claim 2, further comprising a control for operating said circuitry.

4. An apparatus according to claim 3, wherein said precordial electrodes are non-adhesive and wherein operation of said apparatus requires application of human pressure to said support sufficient to retain said selected six precordial electrodes in operative relation with skin of the human chest.

5. An apparatus as called for in claim 4 wherein said support is of a size and shape to have pressure applied thereto by an individual's left arm and left hand, said support having opposed surfaces one of which constitutes an operatively interior surface on which said six precordial electrodes are fixed and another of which constitutes an operatively exterior surface on which the individual applies said pressure.

6. An apparatus as called for in claim 5 wherein said left arm electrode is non-adhesive and is fixed to the operatively exterior surface of said support at a location at which pressure is applied to the support by at least one of the left arm and left hand of the individual so as to enable the left arm electrode to be applied to the individual by engagement with skin of the individual in an operative relation and retention of the operative relation by the pressure applied to the support by the individual.

7. An apparatus as called for in claim 5 wherein said support includes a hollow housing within which said circuitry is mounted.

8. An apparatus as called for in claim 7 wherein said hollow housing is rigid and of a size and shape to extend throughout the human chest.

9. An apparatus as called for in claim 7 wherein said hollow housing is rigid and of a size and shape to receive a first plurality of said precordial electrodes, said support also including a flexible pad-like section connected therewith of a size to receive a remaining plurality of said precordial electrodes, said flexible pad-like section being connected for movement between a storage position wherein the flexible pad-like section is wrapped around the hollow housing to enter therewith within a storage pouch and an operative position extending from said hollow housing so that when the first plurality of electrodes fixed to said hollow housing are retained in operative relation by pressure on said hollow housing from the left hand of the individual, the left arm of the individual can apply pressure to the flexible pad-like section to retain the remaining plurality of electrodes fixed thereto in operative relation.

10. An apparatus as called for in claim 7 wherein said right arm electrode is of a non-adhesive material connected with said circuitry by a wire and is of a size and shape to be conveniently engaged with a right armpit of the individual in an operative relation and to be conveniently retained in said operative relation by pressure from the right arm of the individual.

11. An apparatus as called for in claim 10 wherein said left leg electrode is of a non-adhesive material connected with said circuitry by a wire and is of a size and shape to be conveniently engaged with skin on the individual's waist in an operative position and retained in said operative relation by a garment extending around the individual's waist.

12. An apparatus as called for in claim 1 wherein said circuitry includes a loud speaker and said circuitry is operable to convert the obtained electrical heart activity of the individual into audible signals emitted by said loudspeaker.

13. An apparatus as called for in claim 1 wherein said housing contains a strip chart recorder for producing the twelve-lead electrocardiogram from the obtained electrical heart activity of the individual.

14. An apparatus as called for in claim 1 wherein said circuitry includes a memory within which the obtained electrical heart activity of the individual is stored.

15. An apparatus as called for in claim 1 wherein said support has breast bone locating indicia thereon enabling the individual to locate the support in an operative position with respect to the breast bone of the individual for determining horizontal position of the operative relation of said selected six precordial electrodes.

16. An apparatus as called for in claim 1 wherein said support has a lanyard connected therewith for extension around the neck of the individual for determining a vertical position of the operative relation of said selected six precordial electrodes.

17. An apparatus as called for in claim 1 wherein said right arm electrode is of a non-adhesive material connected with said circuitry by a wire and is of a size and shape to be conveniently engaged with a right armpit of the individual in an operative position and to be conveniently retained in said operative relation by pressure from the right arm of the individual.

18. An apparatus as called for in claim 2 wherein said left leg electrode is of a non-adhesive material connected with said circuitry by a wire and is of a size and shape to be conveniently engaged with the skin of the waist of the individual in an operative position and retained in said operative relation by a garment extending around the waist of the individual.

19. An apparatus as called for in claim 1 wherein said left arm electrode is fixed to said support in a position to be engaged with a left hand of the individual in said operative relation and retained in said operative relation by pressure applied to the support by the left hand of the individual.

20. An apparatus for obtaining electrical heart activity of an individual in a form capable of producing a twelve-lead electrocardiogram of an individual, said apparatus including:

a right arm electrode;

a left arm electrode;

at least one leg electrode;

a portable electrode support having a plurality of contact members fixed thereon, said contact members extending laterally across the support so as to assume different lateral positions across a human chest when said support is positioned over the human chest, a selected number of said contact members being selectively operable to function as six precordial electrodes at positions corresponding to Wilson precordial leads for the individual, wherein at least one of said six precordial electrodes comprise more than one of said contact members; and circuitry provided in electrically connected relation to said contact members and capable of selectively activating said selected number of said contact members to function as said six precordial electrodes at positions corresponding to the Wilson precordial leads for the individual, said circuitry being constructed and arranged to convert the electrical heart activity of the individual into a form capable of producing a twelve-lead electrocardiogram.

21. An apparatus according to claim 20, wherein each of said six precordial electrodes comprises at least two contact members.

22. An apparatus according to claim 21, wherein each of said six precordial electrodes comprise an identical number of contact members.

23. An apparatus according to claim 20, wherein said circuitry is connected to said contact members so as to control operation of said members so that at least one of said contact members is not utilized during operation of said apparatus.

24. An apparatus according to claim 20, wherein said contact members are elongated in shape and are generally disposed in side-by-side relation to one another across said support.

25. An apparatus according to claim 20, wherein said circuitry comprises at least one conductive member for electrically connecting adjacent contact members in electrically conductive relation to one another.

26. An apparatus according to claim 20, further comprising a control for operating said circuitry.

27. An apparatus according to claim 26, wherein said control comprises circuitry for electrically connecting selected adjacent contact members to one another so that they are able to function as said precordial electrodes.

28. A method of obtaining electrical heart activity of an individual in a form capable of producing a twelve-lead electro-cardiogram of an individual comprising the steps of:

applying a right arm electrode, a left arm electrode, and a leg electrode to skin of the individual at locations which enable leads I, II, III, AVR, AVL and AVF to be obtained therefrom;

engaging a plurality of at least seven precordial electrodes extending laterally across an electrode support with skin on the individual's chest so that the precordial electrodes assume different lateral positions across the individual's chest;

operating the right arm electrode, left arm electrode and leg electrode; and operating a selected six of said plurality of precordial electrodes at positions corresponding to six Wilson precordial leads for the individual.

29. A method of obtaining electrical heart activity of an individual in a form capable of producing a twelve-lead electro-cardiogram of an individual comprising the steps of:

applying a right arm electrode, a left arm electrode and a left leg electrode to skin of the individual at locations which enable leads I, II, III, AVR, AVL and AVF to be obtained therefrom;

engaging a plurality of contact members extending laterally across an electrode support with the individual's chest so that the contact members assume different lateral positions across the individual's chest;

operating the right arm electrode, left arm electrode, and leg electrode; and operating a selected number of said contact members to function as six precordial electrodes at positions corresponding to Wilson precordial leads for the individual, wherein at least one of said six precordial leads comprises more than one of said contact members.

* * * * *